United States Patent [19]
Mäyrä-Mäkinen et al.

[11] Patent Number: 5,378,458
[45] Date of Patent: Jan. 3, 1995

[54] *LACTOBACILLUS CASEI* SSP. RHAMOSUS, BACTERIAL PREPARATIONS COMPRISING SAID STRAIN, AND USE OF SAID STRAIN AND PREPARATIONS FOR THE CONTROLLING OF YEAST AND MOULDS

[75] Inventors: Annika Mäyrä-Mäkinen; Tarja Suomalainen, both of Helsinki, Finland

[73] Assignee: Valio Meijerien Keskusosuusliike, Valio Ltd., Helsinki, Finland

[21] Appl. No.: 129,378

[22] Filed: Sep. 30, 1993

Related U.S. Application Data

[63] Continuation of Ser. No. 608, Jan. 5, 1993, abandoned.

[30] Foreign Application Priority Data

Jun. 10, 1992 [FI] Finland ................... 922699

[51] Int. Cl.$^6$ ............... A01N 63/00; C12N 1/20
[52] U.S. Cl. ................... 424/93.3; 424/93.4; 424/93.45; 435/252.9; 435/252.1; 435/252.4; 435/853; 435/856; 435/857; 426/61
[58] Field of Search ............... 435/252.4, 252.9, 252.1, 435/856; 424/93 C, 93 J, 93 N; 426/61

[56] References Cited

U.S. PATENT DOCUMENTS

| | | | |
|---|---|---|---|
| 4,794,080 | 12/1988 | Mays et al. | 435/252.4 |
| 4,842,871 | 6/1989 | Hill | 426/44 |
| 4,863,747 | 9/1989 | Tomes | 426/61 |
| 4,956,177 | 9/1990 | Kung et al. | 435/252.9 |
| 4,981,705 | 1/1991 | Tomes | 426/53 |
| 5,096,718 | 3/1992 | Ayres et al. | 435/252.1 |
| 5,173,319 | 12/1992 | Boudreaux | 426/326 |
| 5,260,061 | 11/1993 | Ayres | 424/115 |

FOREIGN PATENT DOCUMENTS

| | | |
|---|---|---|
| 0302300 | 8/1989 | European Pat. Off. |
| 0408220A2 | 1/1991 | European Pat. Off. |
| 751382 | 4/1979 | U.S.S.R. |

OTHER PUBLICATIONS

Merck Index, 10th Edition, 1983, p. 1127, #7726.

*Primary Examiner*—Marian Knode
*Attorney, Agent, or Firm*—Finnegan, Henderson, Farabow, Garrett & Dunner

[57] ABSTRACT

The invention relates to a novel microorganism strain *Lactobacillus casei* ssp. *rhamnosus* LC-705, DSM 7061, having a yeast and mold controlling effect, to bacterial preparations comprising this strain, alone or in combination with a bacterium of the genus Propionibacterium or another strain of the bacterium *Lactobacillus casei* and/or with conventional agents used for yeast and mold control. The invention also relates to the use of said strain and said bacterial preparations for yeast and mold control and to a method for controlling the growth of yeasts and molds using a bacterial preparation comprising said strain.

22 Claims, No Drawings

LACTOBACILLUS CASEI SSP. RHAMOSUS, BACTERIAL PREPARATIONS COMPRISING SAID STRAIN, AND USE OF SAID STRAIN AND PREPARATIONS FOR THE CONTROLLING OF YEAST AND MOULDS

This application is a continuation, of application Ser. No. 08/000,608, filed Jan. 5, 1993, now abandoned.

FIELD OF THE INVENTION

The present invention relates to a novel microorganism strain having an excellent yeast and mould inhibiting effect, to bacterial preparations comprising said strain alone or in combination with other bacteria and/or additives and to the use of said strain and said bacterial preparations for the inhibition of yeasts and moulds.

BACKGROUND OF THE INVENTION

The shelf-life and utility of foodstuffs and silage, for instance, is often impaired by spoilage caused by yeasts and moulds. Yeasts and moulds may also present problems in the production of foodstuffs, and particularly in the brewing industry the adverse effects are great.

Sorbate and propionate in the form of various alkali salts have mostly been used for the inhibition of yeasts and moulds in foodstuffs. However, there is a tendency to cut back on the use of additives of this kind, and for instance the use of sorbate is prohibited in some European countries. The drawbacks of propionate include the fact that it does not always have a sufficient effect and the fact that it gives a flavour to foodstuffs. Since the consumer attitudes that are increasingly against the use of additives as well as the different foodstuff legislation in different countries must be taken into account, the industry has striven to find natural biopreservatives to replace such additives.

Lactic acid bacteria are known to produce various antimicrobial compounds, such as organic acids, hydrogen peroxide, diacetyl and bacteriocins, and one has attempted to use these as additives for instance to improve the shelf-life of foodstuffs. Commercially available is the product Nisaplin (Aplin & Barrett), comprising purified nisin produced by the bacterium *Lactococcus lactis* and having an effect on gram-positive bacteria only, and thus having no inhibitory effect on the growth of moulds and yeasts.

Efforts have been made to intensively increase the use of lactic acid bacteria for instance in the preservation of forage by testing combinations of lactic acid bacteria mainly with various enzyme preparations. However, such combinations do not have an inhibitory effect on the growth of yeasts and moulds, and therefore they have not provided a solution to the problems caused by yeasts and moulds.

European published application No. 0 302 300 discloses a process for preparing yeast and mould inhibiting products by culturing a Lactobacillus species and isolating the products excreted into the growth medium. These products are stated to be a complex mixture of low molecular weight (MW<1000) compounds, and they are isolated from the growth medium by a multi-step process, which besides extraction steps to be carried out with butanol and ethanol comprises column chromatography and acetone precipitation or dialysis steps. Such a complicated process is not suitable for large-scale production. In said application, spores of *Penicillium oxalicum* are used to show the inhibitory effect.

SUMMARY OF THE INVENTION

The object of the present invention was to find new solutions to the problems caused by yeasts and moulds. When the effect of the antimicrobial factors of various lactic acid and propionic bacteria on the growth of yeasts and moulds was studied, it was unexpectedly found that a novel bacterial strain of the genus Lactobacillus, the *Lactobacillus casei* ssp. *rhamnosus* LC-705 strain, has an excellent inhibitory effect against moulds, for instance moulds of the species Penicillium, Aspergillus, Cladosporium and Fusaarium, and yeasts, for instance Candida species, especially when used as a cell suspension in its fermentation broth.

Furthermore, it was unexpectedly found that the effect of the *Lactobacillus casei* ssp. *rhamnosus* LC-705 strain can be substantially improved by means of a bacterium of the genus Propionibacterium, particularly the *Propionibacterium shermanii* JS strain. The effect can also be improved by using the *Lactobacillus casei* ssp. *rhamnosus* LC-705 strain in combination with another *Lactobacillus casei* strain, particularly the *Lactobacillus casei* ssp. *pseudoplantarum* 1931 strain.

It is also possible to improve the effect of the above strain or the above combinations by means of known substances used for yeast and mould inhibition, such as alkali metal propionate or phenylalanine.

Hence the object of the present invention is a novel bacterial strain of the genus Lactobacillus, *Lactobacillus casei* ssp. *rhamnosus* LC-705, DSM 7061.

Another object of the present invention is a bacterial preparation comprising the *Lactobacillus casei* ssp. *rhamnosus* LC-705 strain, DSM 7061 alone or in combination with a bacterium of the genus Propionibacterium or another strain of the bacterium *Lactobacillus casei*, preferably as a cell suspension in fermentation broth.

Still another object of the present invention a method of inhibiting the growth of yeasts and moulds, the method being characterized by using a bacterial preparation comprising the *Lactobacillus casei* ssp. *rhamnosus* LC-705 strain, DSM 7061, alone or in combination with a bacterium of the genus Propionibacterium or another strain of the bacterium *Lactobacillus casei*, preferably as a cell suspension in fermentation broth.

DETAILED DESCRIPTION OF THE INVENTION

The invention is based on the novel *Lactobacillus casei* ssp. *rhamnosus* LC-705 strain deposited on May 13, 1992 at Deutsche Sammlung von Mikroorganismen und Zellkulturen GmbH (DSM Mascheroder Weg 1 B, D-3300 Braunschweig) with the deposition number DSM 7061 and having the following properties:
gram-positive short rod in chains
homofermentative
good growth at 15°–45° C.
the strain has no proteolytic activity
does not produce ammonia from arginine
catalase-negative
when grown in an MRS broth (LAB M), the strain produces 1.6% lactic acid having an optical activity of the L(+) configuration; the strain decomposes citrate (0.169%), producing diacetyl and acetoin; the strain ferments at least the following carbohydrates (sugars, sugar alcohols): ribose, galactose, D-glucose, D-fructose, D-mannose, L-sorbose, rhamnose, mannitol, sorbitol, methyl-D-glucoside, N-acetylglucosamine, amygdalin, arbutin, esculin, salicin, cellobiose, maltose, lactose, sucrose, trehalose, melezitose, gentiobiose, D-turanose and D-tagatose survives well a salinity of 5% and fairly well a salinity of 10%.

The *Propionibacterium shermanii* JS strain has been deposited on May 13, 1992 at Deutsche Sammlung von Mikroorganismen und Zellkulturen GmbH with deposition number DSM 7067 and has the following properties:

gram-positive, short rod
ferments glucose, fructose, galactose and lactose
ferments lactate well
optimum growth temperature 32° C.

The *Lactobacillus casei* ssp. *pseudoplantarum* 1931 strain is obtainable from the microorganism collection of the Finnish Dairies' Central Co-Operative Society Valio by product number 1931, and it has the following properties:

gram-positive, short rod
facultatively heterofermentative
good growth at 15° 45° C.
no proteolytic activity
does not produce ammonia from arginine
produces D(−) and L(+) lactic acid.

The *Lactobacillus casei* ssp. *rhamnosus* LC-705 strain is produced by growing for instance in a whey-based growth medium for 2 to 3 days at a temperature of 30°–37° C. with or without pH adjustment. The cell-containing fermentation broth is recovered and is used as such, concentrated, or freeze-dried. The concentration may be carried out using microfiltration apparatus or some other corresponding method. The fermentation broth comprising cells of the *Lactobacillus casei* ssp. *rhamnosus* LC-705 strain retains its yeast and mold inhibiting activity when stored cold (at refrigerator temperature) at least for two months, and freeze-dried even longer.

If desired, other bacteria or additives used for yeast and mould inhibition can be added to this cell-containing fermentation broth. When bacteria are employed, said other bacterial strain can be cultured either simultaneously with or separately from the *Lactobacillus casei* ssp. *rhamnosus* LC-705 strain. Simultaneous culturing of the strains is of advantage owing to its simplicity and ease. On the other hand, separate culturing of the strains makes it possible to vary the proportions of the strains to be included in the bacterial preparation, if desired. It is naturally possible to use freeze-dried preparations of both bacteria, which are reconstituted together or separately.

Preferably bacteria of the genus Propionibacterium or cells of another strain of the bacterium *Lactobacillus casei* are added to the fermentation broth comprising the *Lactobacillus casei* ssp. *rhamnosus* LC-705 strain, or the strain is cultured together with a bacterium of the genus Propionibacterium or another strain of the bacterium *Lactobacillus casei*. Preferable preparations are those comprising the *Lactobacillus casei* ssp. *rhamnosus* LC-705 strain and the *Propionibacterium shermanii* JS strain or the *Lactobacillus casei* ssp. *rhamnosus* LC-705 strain and the *Lactobacillus casei* ssp. *pseudoplantarum* 1931 strain.

Most preferable is to add to the fermentation broth comprising the *Lactobacillus casei* ssp. *rhamnosus* LC-705 strain the *Propionibacterium shermanii* JS strain or to culture the two strains together.

A bacterial preparation comprising the *Lactobacillus casei* ssp. *rhamnosus* LC-705 strain alone or in combination with a bacterium of the genus Propionibacterium, for instance the *Propionibacterium shermanii* JS strain, or another strain of the bacterium *Lactobacillus casei*, such as the *Lactobacillus casei* ssp. *pseudoplantarum* 1931 strain, can be used for the prevention of problems caused by yeasts and moulds in many industrial fields, for instance to inhibit the growth of yeasts and moulds during the manufacturing process or to inhibit spoilage caused by yeasts and moulds for example in products of the food industry, brewing industry and forage industry.

The invention will be described in greater detail by means of the following examples. These examples are given only to elucidate the invention and shall not be regarded as restricting the scope thereof.

EXAMPLE 1

Production of the *Lactobacillus casei* ssp. *rhamnosus* LC-705 strain

The *Lactobacillus casei* ssp. *rhamnosus* LC-705 strain was grown on a whey-based growth medium containing 5% of whey permeate (Valio), 2% of casein hydrolysate (Valio) and 1% of yeast extract (Difco) in distilled water. Variation in the nutrient components is possible. During the culturing, the pH of the growth medium was maintained at 4.5 by means of automatic pH adjustment. The culturing was performed as batch culturing at 30°–37° C. for two days, whereafter the cells were recovered in a stage of stationary growth. The bacterial content in the cell-containing fermentation broth was of the order of $10^9$ CFU/ml. The cell-containing fermentation broth may be used as such or concentrated. To prepare the concentrate, the cell-containing fermentation broth is concentrated for instance 10- to 15-fold. The concentration was performed using microfiltration apparatus. Some other corresponding method may also be used. The bacterial content in the concentrate was of the order of $10^{10}$ CFU/ml. The fermentation broth was preserved as such or as a concentrate at about 4° C. or freeze-dried.

EXAMPLE 2

Production of the *Propionibacterium shermanii* JS strain

The *Propionibacterium shermanii* JS strain was grown in a propione fermentation broth for three days at 30° C. in an Erlenmeyer flask. The propione fermentation broth contained 0.5% of tryprone (Difco), 1.0% of yeast extract (Difco) and 4.1% of sodium lactate (30%, Valio) in distilled water. Variation in the nutrient components is possible. When the growth was in a stationary phase, the cells in their fermentation broth were recovered. The *Propionibacterium shermanii* JS content was of the order of $10^{10}$ CFU/ml. The cell-containing fermentation broth can be used as such or concentrated. The concentration can be performed as set forth in Example 1. The cell suspension (fermentation broth with cells) can be preserved as such or concentrated at a temperature of about +4° C.

EXAMPLE 3

Production of a preparation comprising the *Lactobacillus casei* ssp. *rhamnosus* LC-705 strain and the *Propionibacterium shermanii* JS strain The *Lactobacillus casei* ssp. *rhamnosus* LC-705 strain and the *Propionibacterium shermanii* JS strain were inoculated into a whey-based fermentation broth in a ratio of 1:2 or 1:5 depending on the desired propionic acid content of the final product. The composition of the whey-based growth medium was 1) 3.5% of whey permeate, 1.0% of casein hydrolysate, 1.0% of yeast extract and 0.5% of sodium citrate, 2) 3.5% of whey permeate, 1.0% of casein hydrolysate, 1.0% of yeast extract, 0.5% of sodium citrate and 0.5% of sodium chloride or 3) 4.0% of whey permeate, 1.0% of casein hydrolysate and 1.0% of yeast extract.

The strains were cultured for three days at 30° C. maintaining the pH at 4.5 by means of automatic pH adjustment. At the end of the culturing, the fermentation broth with cells was recovered. Such a cell-containing fermentation broth is useful at least for two months when refrigerated.

A cell-containing fermentation broth in which the content of each bacterium was in excess of $10^8$ CFU/ml was used as a preparation inhibiting the growth of moulds and yeasts. The lactic acid content of the preparation was about 0.8–1.3%, the propionic acid content was about 200–550 mg/100 g, depending on the quantity of inoculum employed (for instance 1% or and the acetic acid content was about 150–250 mg/100 g.

The preparation endures heating at 55° C. for 15 minutes without losing its activity entirely, but a treatment at 70° C. clearly impairs its yeast and mould inhibiting activity. The pH of the preparation could be raised to 8 without the activity being impaired.

EXAMPLE 4

Production of a preparation comprising the *Lactobacillus casei* ssp. *rhamnosus* LC-705 strain and the *Lactobacillus casei* ssp. *pseudoplantarum* 1931 strain The *Lactobacillus casei* ssp. *rhamnosus* LC-705 and *Lactobacillus casei* ssp. *pseudoplantarum* 1931 strains were grown for 2 to 3 days at 30°–37° C. on a whey-based growth medium containing 5.0% of whey permeate, 2.0% of casein hydrolysate and 1.0% of yeast extract. The fermentation broth with cells was concentrated with microfiltration apparatus. The fermentation broth was used as such (bacterial content of the order of about $10^9$ CFU/ml) or as concentrated to a bacterial content of about $10^{10}$ CFU/ml for mould and yeast inhibition.

EXAMPLE 5

Inhibition of moulds and yeasts with the *Lactobacillus casei* ssp. *rhamnosus* LC-705 strain Moulds of the genera Penicillium, Aspergillus and Cladosporium isolated from foodstuffs, such as bread and cheese, and Fusarium sp. mould isolated from silage as well as yeasts of the genus Candida isolated from bread were used in the inhibition test.

The moulds and yeasts, except for the mould Fusarium, were regenerated twice before the actual test on malt agar (MEA) slopes. The last culturing was performed at 25° C. for 2 to 3 days. The malt agar contained 2% of malt extract (Difco), 0.1% of peptone (Difco), 2.0% of glucose and 1.5% of agar. The Fusarium mould was regenerated in potato-dextrose agar (PD agar, LAB M).

5 ml of a sterile 0.9% sodium chloride solution was pipetted onto the mould or yeast slope, the growth on the slope being cautiously suspended in said solution by rubbing with a sterile loop. One ml of this suspension was pipetted into 100 ml of sterile 0.9% sodium chloride solution. The mould/yeast content at that stage was $10^5$–$10^6$ CFU/ml. 0.1 ml of this basic suspension was applied to each test dish.

1 ml (or 0.5 ml) of the preparation described in Example 1 (bacterial content about $10^9$ CFU/ml) was pipetted into a dish into which 10 ml of 45° C. PC agar (Plate Count Agar, Difco) was cast, and the agar was allowed to solidify. With Fusarium mould, PD agar (Potato-Dextrose Agar, LAB M) was employed. 0.1 ml of the above-described mould or yeast suspension was pipetted onto the solidified agar and was spread evenly over the dish. The dishes were cultured for 1 day at 30° C. and then for 2 days at 25° C. After the culturing, the dishes were compared with control dishes to which no test preparation had been added. The intensity of the mould or yeast growth as compared with the growth of the controls was read from the dishes.

The inhibitory effect of the *Lactobacillus casei* ssp. *rhamnosus* LC-705 strain in concentrations of 10% and 5% against yeasts and moulds is shown in Table 1. The abbreviations of mould and yeast species in the table denote the moulds Penicillium sp. 1 (16A), Penicillium sp. 2 (114), *Penicillium digitatum* (L5), *Aspergillus niger* (L22), Cladosporium sp. 1 (P1), Penicillium sp. 3 (MZ1) and Fusarium sp. 1 (FH-1) and the yeasts Candida sp. 1 (L9) and *Candida lusitaniae* (L18). The interpretation of the results shown in the table is the following: +++ = very strong mould growth, as in the control; ++ = good mould growth; + = weak mould growth; − = no mould growth. The abbreviation SS used in the table denotes a cell-containing fermentation broth.

TABLE 1

| | Inhibitory effect of the LC-705 preparation | | | | | | | | |
|---|---|---|---|---|---|---|---|---|---|
| | Mould/yeast | | | | | | | | |
| Inhibitor | 114 | 16A | L5 | L9 | L18 | L22 | P1 | MZ1 | FH-1 |
| SS 5% | +++ | ++ | ++ | +++ | + | +++ | +++ | ++ | − |
| SS 10% | +++ | − | ++ | − | − | ++ | − | − | − |
| Control | +++ | +++ | +++ | +++ | +++ | +++ | +++ | +++ | +++ |

The *Lactobacillus casei* ssp. *rhamnosus* LC-705 strain in a concentration of 10% inhibited the Penicillium sp. (16a and MZ1), Cladosporium sp. (P1) and Fusarium (FH-1) moulds and Candida yeasts. On the other hand, a 5% addition inhibited completely the growth of the Fusarium (FH-1) mould only.

EXAMPLE 6

Inhibition of moulds and yeasts with a combination of the *Lactobacillus casei* ssp. *rhamnosus* LC-705 strain and the *Propionibacterium shermanii* JS strain (1:2)

The *Lactobacillus casei* ssp. *rhamnosus* LC-705 and *Propionibacterium shermanii* JS preparation (LC-705 and JS preparation, 1:2) had been produced as described in Example 3. The inhibitory effect of the preparation in a 10% concentration both as a cell suspension and a cell suspension concentrate against yeasts and moulds was studied as described in Example 5 for the strain *Lactobacillus casei* ssp. *rhamnosus* LC-705. The results are shown in Table 2. The abbreviations for the mould and yeast species used in the table and the interpretation of the results presented are as hereinabove in Example 5. The abbreviation SS used in the table denotes a cell-containing fermentation broth, the abbreviation Kons denotes a concentrated cell-containing fermentation broth and the abbreviation SN denotes a fermentation broth with no cells.

TABLE 2

| | Inhibitory effect of the LC-705 and JS (1:2) preparation | | | | | | | |
|---|---|---|---|---|---|---|---|---|
| | Mould/yeast | | | | | | | |
| Inhibitor | 16A | L5 | L9 | L18 | L22 | P1 | MZ1 | FH-1 |
| SS 10% | − | − | − | − | − | − | − | − |
| Kons 10% | +++ | + | +++ | − | − | − | − | − |
| SN 10% | +++ | +++ | +++ | +++ | +++ | +++ | +++ | +++ |
| Control | +++ | +++ | +++ | +++ | +++ | +++ | +++ | +++ |

With the cell-containing fermentation broth (SS), the growth of the moulds Penicillium (16A, L5 and MZ1), Cladosporium (P1), Aspergillus niger (L22) and Fusarium (FH-1) was totally inhibited. Also the growth of yeasts (L9) and (L18) was totally inhibited. Of the dishes treated with a concentrated cell suspension, mould growth was present in two dishes and yeast growth in one dish. The supernatant of the cell culture, wherefrom the cells had been centrifuged off (SN), had no inhibitory effect on the growth of moulds and yeasts.

EXAMPLE 7

Inhibition of moulds and yeasts with a combination of the *Lactobacillus casei* ssp. *rhamnosus* LC-705 strain and the *Propionibacterium shermanii* JS strain (1:5)

The *Lactobacillus casei* ssp. *rhamnosus* LC-705 and *Propionibacterium shermanii* JS preparation (LC-705 and JS preparation, 1:5) had been produced as described in Example 3. The inhibitory effect of the preparation in a 5% concentration both as a cell suspension and a cell suspension concentrate against yeasts and moulds was studied as described in Example 5 for the strain *Lactobacillus casei* ssp. *rhamnosus* LC-705. The results are shown in Table 3. The abbreviations for the mould and yeast species used in the table, the interpretation of the results presented and the other abbreviations are as hereinabove in Examples 5 and 6.

TABLE 3

| | Inhibitory effect of the LC-705 and JS (1:5) preparation | | | | | | | |
|---|---|---|---|---|---|---|---|---|
| | Yeast/mould | | | | | | | |
| Inhibitor | 114 | L5 | L9 | L18 | L22 | P1 | MZ1 | FH-1 |
| SS 5% | + | + | − | + | − | − | − | − |
| SN 10% | +++ | +++ | +++ | +++ | +++ | +++ | +++ | ++ |
| Control | +++ | +++ | +++ | +++ | +++ | +++ | +++ | +++ |

With the cell-containing fermentation broth (SS), the growth of the moulds Aspergillus niger (L22), Penicillium sp. (MZ1), Cladosporium sp. (Pi) and Fusarium sp. (FH-1) was totally inhibited. Also the growth of the yeast Candida sp. 1 (L9) was totally inhibited. The growth of the moulds Penicillium sp. 2 and *Penicillium digitatum* (114 and L5) and the yeast *Candida lusitaniae* (L18) was clearly impaired. The supernatant of the cell culture, wherefrom the cells had been centrifuged off (SN), had no inhibitory effect on the growth of moulds and yeasts.

EXAMPLE 8

Inhibition of moulds and yeasts with a combination of the *Lactobacillus casei* ssp. *rhamnosus* LC-705 strain and the *Propionibacterium shermanii* JS strain (1:1)

The *Lactobacillus casei* ssp. *rhamnosus* LC-705 strain and the *Propionibacterium shermanii* JS strain were cultured as described in Example 1 and Example 2, respectively, whereafter the fermentation broths with cells were combined in a ratio of 1:1. The inhibitory effect of the compound against moulds and yeasts was studied as described in Example 5 for the strain *Lactobacillus casei* ssp. *rhamnosus* LC-705. The results are shown in Table 4. The abbreviations for the mould and yeast species used in the table, the interpretation of the results presented and the other abbreviations are as hereinabove in Example 5.

TABLE 4

| | Inhibitory effect of the LC-705 and JS (1:1) preparation | | | | |
|---|---|---|---|---|---|
| | Mould/yeast | | | | |
| Inhibitor | 114 | L9 | L22 | P1 | MZ1 |
| SS 5% | ++ | ++ | + | + | + |
| SS 10% | + | − | − | − | − |
| Control | +++ | +++ | +++ | +++ | +++ |

As a 10% addition, the preparation inhibited the growth of the yeast Candida sp. 1 (L9) and the growth of the moulds Aspergillus niger (L22), Cladosporium sp. 1 (P1) and Penicillium sp. 3 (MZ1) totally in dish tests. At a concentration of 5%, the preparation clearly retarded the growth of the moulds L22, P1 and MZ.

EXAMPLE 9

Inhibition of moulds and yeasts with a combination of the *Lactobacillus casei* ssp. *rhamnosus* LC-705 strain and the *Lactobacillus casei* ssp. *pseudoplantarum* 1931 strain The *Lactobacillus casei* ssp. *rhamnosus* LC-705 and *Lactobacillus casei* ssp. *pseudoplantarum* 1931 preparation (LC-705 and 1931 preparation, 1:1) had been produced as described in Example 4. The inhibitory effect of the preparation at a 10% concentration both as a cell suspension and a cell suspension concentrate against yeasts and moulds was studied as described in Example 5 for the strain *Lactobacillus casei* ssp. *rhamnosus* LC-705. The results are shown in Table 5. The abbreviations for the mould and yeast species used in the table, the interpretation of the results presented and the other abbreviations are as hereinabove in Examples 5 and 6.

TABLE 5

Inhibitory effect of the LC-705 and 1931 (1:1) preparation

| Inhibitor | Mould/yeast | | | | | | | |
|---|---|---|---|---|---|---|---|---|
| | 114 | 16A | L5 | L9 | L18 | L22 | P1 | MZ1 |
| SS 10% | ++ | + | ++ | − | − | ++ | − | − |
| Kons 10% | − | − | − | − | − | − | − | − |
| SN 10% | +++ | +++ | +++ | +++ | +++ | +++ | +++ | +++ |
| Control | +++ | +++ | +++ | +++ | +++ | +++ | +++ | +++ |

Of these preparations, the most effective in inhibiting moulds and yeasts was the concentrated cell-containing fermentation broth (cell concentrate). The cell-containing fermentation broth as such had a notably weaker activity than the concentrate had, and the supernatant of the cell culture, wherefrom the cells had been centrifuged off (SN), had no effect of inhibiting mould and yeast growth.

EXAMPLE 10

Use of preparations comprising the *Lactobacillus casei* ssp. *rhamnosus* LC-705 strain in the production of pre-dried silage The *Lactobacillus casei* ssp. *rhamnosus* LC-705 strain and the *Propionibacterium shermanii* JS strain were grown in a fermentor for 3 days at 30° C. at pH 4.5. The composition of the growth medium was the following: 4% of whey permeate, 1% of casein hydrolysate and 1% of yeast extract. A cell suspension (fermentation broth with cells) having a cell content of $1.2 \times 10^9$/ml for LC-705 and $1.1 \times 10^9$/ml for JS was used as the preparation.

The *Lactobacillus casei* ssp. *rhamnosus* LC-705 strain and the *Lactobacillus casei* ssp. *pseudoplantarum* 1931 strain were grown together to a total content of about $2 \times 10^{11}$ CFU/ml in a fermentor for 2 days at 30° C. at pH 4.5. The composition of the growth medium was the following: 4% of whey permeate, 1% of casein hydrolysate, 1% of yeast extract and 0.1% of Tween 80. A cell concentrate having a cell content of $2 \times 10^{11}$ CFU/ml was used as the preparation.

The *Lactobacillus plantarum* LB 7.5-5 strain was grown in a fermentor on a H growth medium containing 5% of whey permeate, 0.5% of casein hydrolysate, 0.25% of yeast extract, 0.05 g/l of $MnSO_4$ and 0.1% of Tween 80, for 20 hours at 30° C. at pH 5.4. A cell suspension having a cell content of $7 \times 10^{10}$ CFU/ml was used as the preparation.

A Fusarium mould (F67) was grown on a PD agar slope for 3 days at 25° C., whereafter the growth was suspended in a sterile 0.9% sodium chloride solution. The mould content in the suspension was about $10^6$ CFU/ml. In the silage the content was about 10–100 CFU/g.

The preparations were mixed with pre-dried silage (15 kg) by spraying, whereafter the silage was compactly packed in silos. The results are shown in Tables 6 to 8 hereinbelow. Silo 1 is a control silo with no inoculum. Silo 2 is a sample treated with preparation LC-705+JS (2.5%) and mould F67. Silo 3 is a sample treated with preparation LC-705+1931 (2.5%) and mould F67. Silo 4 is a sample treated with preparation LB 7.5-5 (2.5%) and mould F67. Silo 5 is a sample treated with mould F67 (10–100 CFU/ml). Samples were taken from the silos immediately after the addition before the silos were closed, and ten weeks after the addition.

The yeasts and moulds, except for the mould Fusarium, were determined with HDK growth medium having the following composition: 0.5% of yeast extract, 2% of dextrose and 100 mg/ml of chloramphenicol in 1.5% agar. The mould Fusarium was determined with PD agar. Coliform bacteria were determined with VRB agar (Violet Red Bile Agar, LAB M), lactic acid bacteria with MRS agar and the propionic bacteria with a sodium lactate growth medium having the following composition: 0.5% of trypton (Difco), 1.25% of 30% sodium lactate and 1% of yeast extract in 1.5% agar. Total bacteria were determined with PC agar.

TABLE 6

Initial microbial content in silage (CFU/g)

| Silo | Coli | L.a. bact. | Tot. bact. | Prop. bact. |
|---|---|---|---|---|
| 1. | $8.4 \times 10^7$ | $1.6 \times 10^7$ | $2.0 \times 10^8$ | * |
| 2. | $1.0 \times 10^8$ | $3.8 \times 10^7$ | $2.2 \times 10^8$ | $2.0 \times 10^7$ |
| 3. | $4.1 \times 10^8$ | $2.0 \times 10^9$ | $2.7 \times 10^9$ | * |
| 4. | $1.9 \times 10^8$ | $7.1 \times 10^8$ | $1.0 \times 10^9$ | * |
| 5. | $3.4 \times 10^8$ | $2.4 \times 10^7$ | $4.5 \times 10^8$ | * |

* = could not be shown

TABLE 7

Final microbial content in silage (CFU/g)

| Silo | Coli | L.a. bact. | Tot. bact. |
|---|---|---|---|
| 1. | <10 | $6.1 \times 10^7$ | <1000 |
| 2. | <10 | $1.0 \times 10^9$ | <1000 |
| 3. | <10 | $1.2 \times 10^9$ | <1000 |
| 4. | <10 | $1.6 \times 10^8$ | <1000 |
| 5. | <10 | $9.0 \times 10^7$ | <1000 |

TABLE 8

Yeast and mould content in silage (CFU/g)

| | Yeasts | | | Moulds | | |
|---|---|---|---|---|---|---|
| | Time | | | | | |
| Silo | 0 w. | 10 w. | 11 w. | 0 w. | 10 w. | 11 w. |
| 1. | $2.6 \times 10^5$ | $2 \times 10^4$ | $5 \times 10^8$ | $2.8 \times 10^5$ | <1000 | <1000 |
| 2. | $1.9 \times 10^5$ | <1000 | $3 \times 10^5$ | $1.8 \times 10^5$ | <1000 | <1000 |
| 3. | $5.0 \times 10^5$ | <1000 | $1 \times 10^7$ | $3.1 \times 10^5$ | <1000 | $3 \times 10^6$ |
| 4. | $6.0 \times 10^4$ | $1.9 \times 10^5$ | $7 \times 10^8$ | $1.6 \times 10^5$ | <1000 | $2 \times 10^8$ |
| 5. | $2.6 \times 10^5$ | $2.6 \times 10^6$ | $5 \times 10^8$ | $8.2 \times 10^5$ | <1000 | $2 \times 10^4$ |

After storage of ten weeks, there were differences in the appearance of the opened silos. A visible white surface growth had formed in all silos except in silo 2, said growth obviously being yeast growth. Silos 1 and 5 contained the most yeast growth. According to microbiological determination (sensitivity of determination<1000), silo 2 and silo 3 contained no aerobic bacteria or yeasts and moulds. Silos 1, 4 and 5 had aerobic microbes at the time of opening.

According to determination made from the silos one week later (11 weeks from the start of the test), a yeast growth had developed in all of the silos. The yeast content was lowest in silo 2. A mould growth had developed in silos 3, 4 and 5. The inoculum added to silo 2 had inhibited the growth of mould.

EXAMPLE 11

Use of preparations comprising the *Lactobacillus casei* ssp. *rhamnosus* LC-705 strain in the production of pre-dried silage (dry matter content 25–50%)

The *Lactobacillus casei* ssp. *rhamnosus* LC-705 strain and the *Propionibacterium shermanii* JS strain were grown in a fermentor for 3 days at 30° C. at pH 4.5. The composition of the growth medium was the following: 3.5% of whey permeate, 1.5% of casein hydrolysate, 1.0% of yeast extract and 0.5% of sodium citrate (Difco). A cell suspension having a cell content of $5 \times 10^8$ for LC-705 and $2 \times 10^{10}$/ml for JS was used as the preparation.

2.5% of the preparation was added by spraying to pre-dried round-baled silage having a dry matter content of 40%. Samples were taken from the round bale with a sterile bore in accordance with a timetable. Silage preserved without a preservative was used as a reference sample. The microbiological results are shown in Tables 9 and 10 below.

The microbial determinations were made by the methods described in Example 10 above.

TABLE 9

Microbiological results of round-baled predried silage treated with the preparation (CFU/g)

| Time | L. a. bact. | Yeasts | Moulds | Coli |
|---|---|---|---|---|
| 0 | $3.8 \times 10^5$ | $2.1 \times 10^6$ | $9.0 \times 10^5$ | $6.7 \times 10^6$ |
| 6 | $2.2 \times 10^9$ | 300 | 0 | $5.9 \times 10^6$ |
| 13 | $1.9 \times 10^9$ | 0 | 0 | 700 |
| 22 | $1.1 \times 10^9$ | 0 | 0 | 3000 |
| 41 | $6.3 \times 10^8$ | 0 | 0 | 0 |
| 62 | $4.3 \times 10^8$ | 0 | 0 | 0 |
| 99 | $1.7 \times 10^8$ | 0 | 0 | 0 |
| 125 | $2.1 \times 10^7$ | 0 | 0 | 0 |

TABLE 10

Microbiological results of reference silage (no preservatives) (CFU/g)

| Time | L. a. bact. | Yeasts | Moulds | Coli |
|---|---|---|---|---|
| 7 | $7.4 \times 10^6$ | 900 | 300 | $9.3 \times 10^6$ |
| 14 | $1.8 \times 10^7$ | 0 | 20 | $5.5 \times 10^6$ |
| 23 | $5.0 \times 10^5$ | 100 | 80 | 400 |
| 42 | $1.1 \times 10^7$ | 7300 | 3200 | $1.3 \times 10^5$ |
| 63 | $2.2 \times 10^6$ | 0 | 6000 | $3.0 \times 10^5$ |
| 100 | $2.8 \times 10^5$ | 2300 | $1.6 \times 10^4$ | $1.1 \times 10^5$ |
| 126 | $2.1 \times 10^6$ | 30 | 10 | $7.2 \times 10^4$ |

No moulds and yeasts could be detected in the pre-dried round-baled silage treated with the preparation after the first week, whereas the yeast content in the reference silage varied between 0 and 7300 CFU/g and the mould content between 10 and 1600 CFU/g during the preservation time. The microbiological quality of the silage treated with the preparation comprising the *Lactobacillus casei* ssp. *rhamnosus* LC-705 strain as a whole was superior to that of the silage with no preservative.

EXAMPLE 12

Use of a preparation comprising the *Lactobacillus casei* ssp. *rhamnosus* LC-705 strain for the inhibition of moulding of sour bread The *Lactobacillus casei* ssp. *rhamnosus* LC-705 strain was the *Propionibacterium shermanii* JS strain were inoculated in a ratio of 1:5 into a whey-based growth medium containing 3.5% of whey permeate, 1.0% of casein hydrolysate, 1.0% of yeast extract and 0.5% of sodium citrate. The strains were cultured for 3 days at 30° C. at pH 4.5. The fermentation broth with cells was recovered and added as such to a sour bread dough. The bacterial content of the preparation were $3 \times 10^9$ CFU/ml for LC-705 and $4 \times 10^9$ CFU/ml for JS.

The preparation was added in an amount of 10%, and the addition was taken into account in the water quantity in the dough.

A manufacturer's commercial sour bread was used as reference bread. The bread was baked into toast bread; 24 of the loaves were stored whole and 86 loaves were sliced. The moulding of the bread loaves was observed visually for 21 days.

The results are shown in Table 11.

TABLE 11

| | Moulding of sour bread loaves | | | |
|---|---|---|---|---|
| | Reference loaves | | Test loaves | |
| days | whole | sliced | whole | sliced |
| 5 | 0/24 | 0/5 | 0/24 | 0/5 |
| 6 | 3/24 | 0/5 | 0/24 | 0/5 |
| 7 | 8/24 | 2/5 | 0/24 | 0/5 |
| 10 | 11/24 | 5/5 | 1/24 | 2/5 |
| 11 | 15/24 | 5/5 | 2/24 | 1/5 |
| 12 | 15/24 | | 3/24 | 2/5 |
| 13 | 15/24 | | 3/24 | 5/5 |
| 14 | 16/24 | | 5/24 | 3/5 |
| 17 | 16/24 | | 13/24 | 5/5 |
| 18 | 16/24 | | 14/24 | 4/5 |
| 20 | 19/24 | | 15/24 | 4/5 |
| 21 | 19/24 | | 15/24 | 29/31 |

The reference loaves were spoiled more rapidly than the loaves treated with the preparation. The first mould was detected in the reference loaves after 6 days and in the test loaves only after 10 days. Of all reference loaves, almost 50% were spoiled after 10 days, whereas 50% of the loaves treated with the preparation were spoiled only after 17 days. Of the sliced loaves, the reference loaves were spoiled considerably more rapidly. Of the 5 packages of reference loaves which were observed daily, all 5 were spoiled already after 10 days and 11 days, and thus the observation of the reference loaves was discounted. Of the loaves to which the preparation had been added, all 5 packages were spoiled for the first time after 13 days, but of the loaves of the following day only 3 packages were spoiled.

EXAMPLE 13

Use of a preparation comprising the *Lactobacillus casei* ssp. *rhamnosus* LC-705 strain for the inhibition of moulding of wheat bread The *Lactobacillus casei* ssp. *rhamnosus* LC-705 strain and the *Propionibacterium shermanii* JS strain were inoculated in a ratio of 1:5 into a whey-based growth medium containing 3.5% of whey permeate, 1.0% of casein hydrolysate, 1.0% of yeast extract and 0.5% of sodium citrate. The strains were cultured for 3 days at 30° C. at pH 4.5. The fermentation broth with cells was concentrated and freeze-dried. The bacterial content of the freeze-dried preparation was 2×10¹¹ CFU/g for LC-705 and JS.

The preparation was added to the dough in amounts of 0.1%, 0.25% and 0.5% of the total volume of the dough. Similar manufacturer's commercial wheat bread was used as reference bread. The bread was baked into toast bread (17 loaves). The moulding of the bread loaves was observed visually for 9 days. Also the taste of the bread was evaluated.

The results are shown in Table 12.

TABLE 12

| Time days | Moulding of wheat bread loaves | | | |
|---|---|---|---|---|
| | Moulded loaves/17 loaves Reference loaves | Test loaves | | |
| | | 0.1% | 0.25% | 0.5% |
| 4 | 0 | 0 | 0 | 0 |
| 5 | 1 | 0 | 2 | 1 |
| 6 | 9 | 1 | 3 | 1 |
| 7 | 16 | 7 | 4 | 4 |
| 8 | 17 | 16 | 7 | 12 |
| 9 | 17 | 17 | 12 | 14 |

The reference loaves were spoiled more rapidly than the wheat loaves treated with the preparation. Of the wheat loaves treated with the preparation, the ones with 0.25% of preparation added were best preserved. More than 50% of these loaves were not moulded until after 8 days, whereas more than 50% of the reference loaves were moulded after 6 days. Also the total mould content in the bread loaves treated with the preparation was smaller than in the reference loaves. The preparation also improved the taste and aroma of the wheat bread.

We claim:

1. A method of inhibiting the growth of yeasts and moulds comprising contacting a material with an effective amount of a bacterial preparation comprising *Lactobacillus casei* ssp. *rhamnosus* LC-705 strain, DSM 7061.

2. The method of inhibiting the growth of yeasts and moulds as claimed in claim 1, wherein the bacterial preparation comprising the *Lactobacillus casei* ssp. *rhamnosus* LC-705 strain, DSM 7061, is in a cell suspension.

3. A method of inhibiting the growth of yeasts and moulds comprising contacting a material with an effective amount of a bacterial preparation comprising *Lactobacillus casei* ssp. *rhamnosus* LC-705 strain, DSM 7061, and a bacterium of the genus Propionibacterium.

4. The method of inhibiting the growth of yeasts and moulds as claimed in claim 3, wherein the bacterial preparation comprises the *Lactobacillus casei* ssp. *rhamnosus* LC-705 strain, DSM 7061, and *Propionibacterium shermanii* JS, DSM 7067.

5. The method of inhibiting the growth of yeasts and moulds as claimed in claim 4, wherein the bacterial preparation is in a cell suspension in fermentation broth.

6. A method of inhibiting the growth of yeasts and moulds comprising contacting a material with an effective amount of a bacterial preparation comprising *Lactobacillus casei* ssp. *rhamnosus* LC-705 strain, DSM 7061, and another strain of the bacterium *Lactobacillus casei*.

7. A biologically pure culture of *Lactobacillus casei* ssp. *rhamnosus* LC-705, DSM 7061 having yeast and mold inhibiting properties.

8. A bacterial preparation having yeast and mold inhibiting properties comprising the *Lactobacillus casei* ssp. *rhamnosus* LC-705 strain, DSM 706and a carrier.

9. The bacterial preparation as claimed in claim 8 comprising the *Lactobacillus casei* ssp. *rhamnosus* LC-705 strain, DSM 7061, as a cell suspension in fermentation broth.

10. The bacterial preparation as claimed in claim 9 wherein the cell suspension is concentrated.

11. The bacterial preparation as claimed in claim 9 wherein the cell suspension is freeze-dried.

12. The bacterial preparation as claimed in claim 2 comprising additional conventional agents used for yeast and mould inhibition.

13. The bacterial preparation as claimed in claim 12 wherein the additional conventional agents used for mold and yeast inhibition are selected from the group consisting of propionate and phenylalanine.

14. A bacterial preparation having yeast and mold inhibiting properties comprising the *Lactobacillus casei* ssp. *rhamnosus* LC-705 strain DSM 7061, in combination with a bacterium of the genus Propionibacterium.

15. The bacterial preparation as claimed in claim 14 comprising the *Lactobacillus casei* ssp. *rhamnosus* LC-705 strain, DSM 7061 together with the *Propionibacterium shermanii* JS, DSM 7067.

16. A bacterial preparation as claimed in claim 15 comprising the *Lactobacillus casei* ssp. *rhamnosus* LC-705 strain, DSM 7061, together with the *Propionibacterium shermanii* JS, DSM 7067, as a cell suspension in fermentation broth.

17. A bacterial preparation as claimed in claim 14 comprising additional conventional agents used for yeast and mould inhibition.

18. The bacterial preparation as claimed in claim 17 wherein the additional conventional agents used for mold and yeast inhibition are selected from the group consisting of propionate and phenylalanine.

19. A bacterial preparation having yeast and mold inhibiting properties comprising the *Lactobacillus casei* ssp. *rhamnosus* LC-705 strain, DSM 7061, in combination with another strain of the bacterium *Lactobacillus casei*.

20. A bacterial preparation as claimed in claim 19 comprising the *Lactobacillus casei* ssp. *rhamnosus* LC-705 strain, DSM 7061, as a cell suspension in fermentation broth in combination with another strain of the bacterium *Lactobacillus casei*.

21. A bacterial preparation as claimed in claim 19 comprising additionally conventional agents used for yeast and mould inhibition.

22. The bacterial preparation as claimed in claim 21 wherein the additional conventional agents used for mold and yeast inhibition are selected from the group consisting of propionate and phenylalanine.

* * * * *

UNITED STATES PATENT AND TRADEMARK OFFICE
CERTIFICATE OF CORRECTION

PATENT NO. : 5,378,458
DATED : January 3, 1995
INVENTOR(S) : Mayra-Makinen et al.

It is certified that error appears in the above-indentified patent and that said Letters Patent is hereby corrected as shown below:

Claim 8, col. 14, line 8, "706and" should read --7061 and--.

Claim 12, col. 14, line 17, "claim 2" should read --claim 8--.

Claim 16, col. 14, line 32, "A" should read --The--.
Claim 17, col. 14, line 37, "A" should read --The--.
Claim 20, col. 14, line 50, "A" should read --The--.
Claim 21, col. 14, line 55, "A" should read --The--.

Signed and Sealed this

Twenty-fifth Day of July, 1995

Attest:

BRUCE LEHMAN

Attesting Officer          Commissioner of Patents and Trademarks